(12) United States Patent
Dmuschewsky et al.

(10) Patent No.: US 9,655,632 B2
(45) Date of Patent: May 23, 2017

(54) DEVICE FOR DEFINING A CUTTING PLANE FOR A BONE RESECTION

(71) Applicant: WALDEMAR LINK GMBH & CO. KG, Hamburg (DE)

(72) Inventors: Klaus Dmuschewsky, Hamburg (DE); Amos Balzarini, Norderstedt (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 368 days.

(21) Appl. No.: 14/359,220

(22) PCT Filed: Nov. 2, 2012

(86) PCT No.: PCT/EP2012/071689
§ 371 (c)(1),
(2) Date: May 19, 2014

(87) PCT Pub. No.: WO2013/075925
PCT Pub. Date: May 30, 2013

(65) Prior Publication Data
US 2014/0324054 A1    Oct. 30, 2014

(30) Foreign Application Priority Data
Nov. 23, 2011    (EP) .................................. 11190415

(51) Int. Cl.
*A61B 17/15*    (2006.01)
*A61B 17/17*    (2006.01)
(Continued)

(52) U.S. Cl.
CPC ........ *A61B 17/1764* (2013.01); *A61B 17/155* (2013.01); *A61B 17/157* (2013.01); *A61B 2090/067* (2016.02); *A61F 2002/4668* (2013.01)

(58) Field of Classification Search
CPC ..... A61B 17/15; A61B 17/154; A61B 17/155; A61B 17/1764
(Continued)

(56) References Cited

U.S. PATENT DOCUMENTS

| 4,952,213 A | 8/1990 | Bowman et al. |
| 5,228,459 A | 7/1993 | Caspari |

(Continued)

FOREIGN PATENT DOCUMENTS

| EP | 1144956 | 6/2000 |
| EP | 1040791 | 10/2000 |

(Continued)

*Primary Examiner* — Zade Coley
(74) *Attorney, Agent, or Firm* — Sand & Sebolt

(57) ABSTRACT

An adjustable device for defining a cutting plane for bone resection comprising a base positionable on the bone and a cut-guiding element placeable on the base. The cut-guiding element includes a cut-guiding structure for guiding a cutting tool in the cutting plane, the cut-guiding element being tiltable relative to the base about at least one first axis by an adjustable tilt mechanism to adjust the angle of the cutting plane. The tilt mechanism includes a rectilinear guide and a slide that is linearly displaceable along the guide in the longitudinal direction. The tilt mechanism includes a guide portion relative to which an effective portion of the slide is displaced; the guide portion and the effective portion having interacting structures forming a sliding guide effective at a right angle to the longitudinal direction.

12 Claims, 10 Drawing Sheets

(51) Int. Cl.
*A61F 2/46* (2006.01)
*A61B 90/00* (2016.01)

(58) Field of Classification Search
USPC .......................................................... 606/89
See application file for complete search history.

(56) References Cited

U.S. PATENT DOCUMENTS

| | | | | |
|---|---|---|---|---|
| 5,342,368 A * | 8/1994 | Petersen | ............... | A61B 17/157 606/87 |
| 5,749,876 A | 5/1998 | Duvillier et al. | | |
| 6,077,270 A * | 6/2000 | Katz | ................... | A61B 17/154 606/102 |
| 7,374,563 B2 * | 5/2008 | Roger | .................. | A61B 17/155 606/88 |
| 7,628,793 B2 * | 12/2009 | Calton | ................. | A61B 17/157 606/88 |
| 8,974,459 B1 * | 3/2015 | Axelson, Jr. | ......... | A61B 17/155 606/86 R |
| 2010/0121334 A1 * | 5/2010 | Couture | ............... | A61B 17/155 606/87 |

FOREIGN PATENT DOCUMENTS

| | | | | |
|---|---|---|---|---|
| EP | 1040791 A1 | 10/2000 | | |
| EP | 1269924 | 1/2003 | | |
| EP | 1269924 A1 | 1/2003 | | |
| EP | 1444957 | 8/2004 | | |
| EP | 1444971 | 8/2004 | | |
| WO | WO 2009006741 A1 * | 1/2009 | ........... | A61B 17/155 |

\* cited by examiner

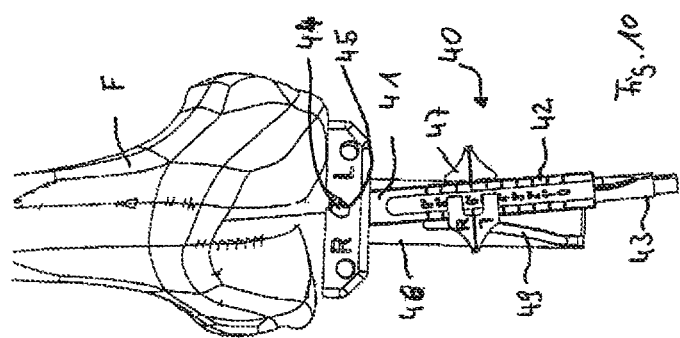
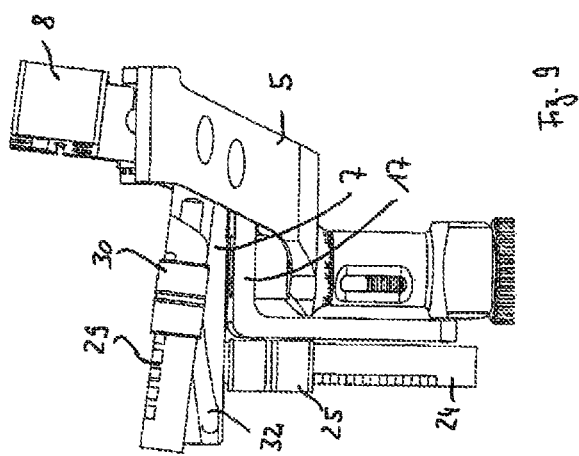

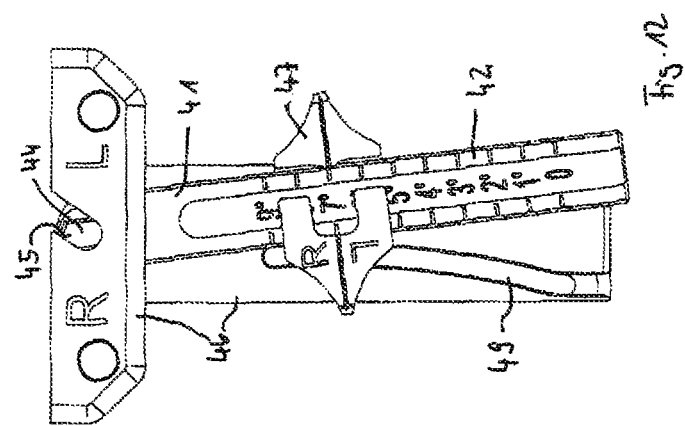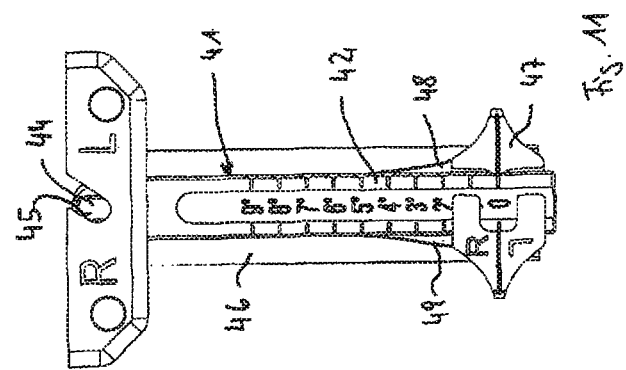

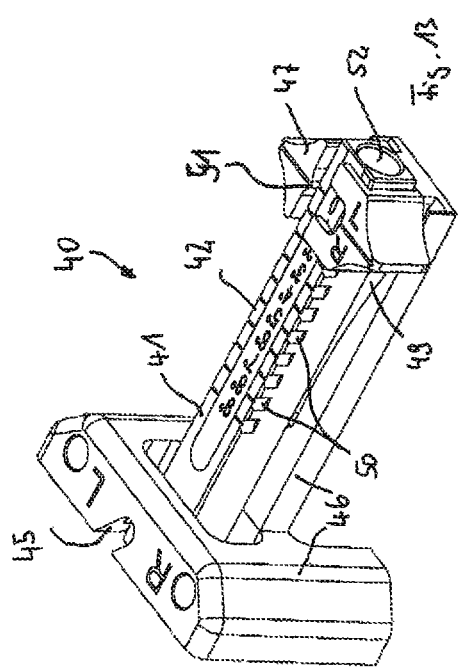

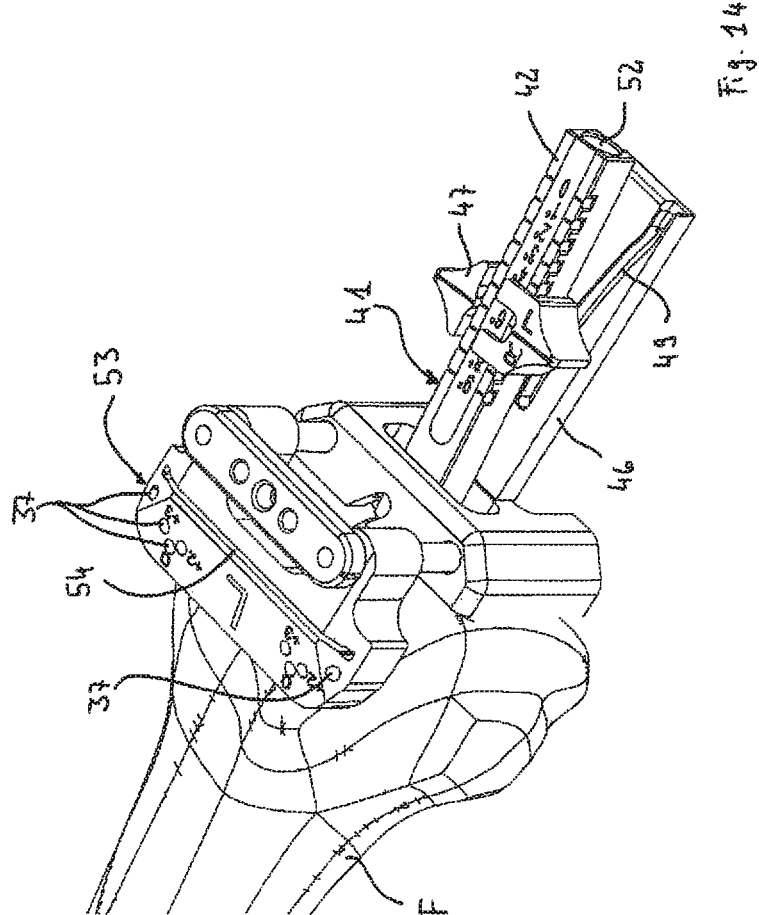

DEVICE FOR DEFINING A CUTTING PLANE FOR A BONE RESECTION

TECHNICAL FIELD

The present invention relates to a device for defining a cutting plane for bone resection which includes a base body that can be positioned on the bone as well as a cut-guiding body which can be attached to the base body in a variable position and has a cut-guiding structure for guiding a cutting tool in the cutting plane, where the cut-guiding body can be tilted relative to the base body by means of a first adjustable tilt mechanism about at least one axis for an angle adjustment of the cutting plane.

PRIOR ART

In medicine, in particular for the use of joint endoprostheses in orthopedic surgery, resection cuts are made to remove the worn regions of the bones involved in the respective joint and to create a defined binding geometry for the joint endoprosthesis parts to be used. It is important for the resection cuts to be guided precisely, so that an endoprosthetic replacement will permit optimal function with regard to the geometry in which it is positioned in the patient's body and will restrict the patient as little as possible with regard to freedom of movement. This is true not only in the field of knee endoprosthesis, where appropriate care must be taken in resection of the distal femur component and the proximal tibia plateau in order not to alter the postoperative position and spatial orientation of the leg having the endoprosthesis with respect to the initial situation, at least not in a manner that would negatively impact the patient. In addition to retaining the leg length, one should also select here the correct adjustment of the varus/valgus angle as well as the so-called slope angle, i.e., the angle of the axis of the plane that is tilted about an axis with respect to the horizontal, such that this axis is the connecting axis of both knees with the legs parallel and/or is an axis running parallel to this connecting axis. All these parameters—in conjunction with the geometry of the respective components of the endoprosthesis—are determined by the position of the cutting planes of the respective bone resections and thus the position of the binding planes for the part of the endoprosthesis to be attached to this cutting plane.

However, an accurate adjustment of the cutting plane with respect to a longitudinally displaceable spacing and also with respect to at least one tilt plane is also important in other bone resections, for example, in resection of the head of the humerus in the event of surgical treatment with a shoulder endoprosthesis joint.

Accordingly, in such operations, the bone resection cuts are not guided free hand, but instead the position and location of the cutting plane are first mapped using appropriate auxiliary equipment on the exposed bone and then the resection is performed using a cutting tool guided in the cutting guide structure of such a device.

Such devices include a base body that can be positioned on the bone and a cut-guiding element on which the cut-guiding structure is formed. The base body and the cut-guiding element may be shifted relative to one another for a targeted adjustment of the cutting plane, in particular being tilted about at least one first axis for tilting the cutting plane. During surgery, the base body is often first secured on the bone, for example, by means of fixation pins, which are inserted into the holes created in the bone, and then the cut-guiding structure is adjusted for creating the desired resection in the proper cutting plane through appropriate adjustment and/or positioning of the cut-guiding element. This cut-guiding element can also be secured on the bone with many known devices, for example, by means of fastening pins inserted into holes created in the bone and secured there. EP 1 144 956 A1, for example, describes an appropriate device that is equipped and intended specifically for defining a cutting plane during tibial resection. EP 1 269 924 A1 and EP 1 444 957 A1, respectively, describe corresponding devices and their usability for bone resection of the proximal tibia plateau as well as the distal femur plateau. The device in the latter document has such a device with which, starting from a base body secured on the bone, a cut-guiding body disposed thereon by means of various bearing blocks may be tilted about a first plane axis and can also be tilted about a second axis perpendicular to the first axis and finally, is also adjustable with regard to the height, i.e., the distance from the base body. With regard to use for resection of the proximal tibia plateau in particular, the approach disclosed there offers a substantial advantage in comparison with the approach disclosed in EP 1 040 791 A1, for example, in which one of the aforementioned angles, in particular the slope angle, can be set by setting the locking position of a guiding and retaining rod in the area of a foot clamp to be secured on the patient's foot at his ankle. It is usually quite difficult to tightly secure the foot clamp there because excessively high retaining forces cannot be applied, so as not to endanger the blood supply to the foot. Accordingly, it is often not easy to keep such foot clamps stable and thus also, by making an adjustment in this area, to make a corresponding, accurate and precision adjustment of the angular position. As already explained, there is a better solution to this according to EP 1 444 971 A1 because an adjustment of all parameters is performed for the definition of the position of the cutting plane in a region directly adjacent to the location of the resection cut to be created, i.e., by means of a base body, which is itself to be secured on the bone to be resected.

However, the device disclosed in this document is comparatively user-unfriendly, in particular with regard to the adjustment of the tilt(s) of the cutting plane(s) with respect to the slope angle and/or the varus/valgus angle. In addition, screws are used to secure the angular positions of the cutting plane, but such screws can become loosened, in particular when vibrations occur, such as vibrations generated by a cutting tool used to perform the bone resection and transmitted to the cut-guiding element by means of the cut-guiding slot provided as a cut-guiding structure. There is therefore the risk of a faulty adjustment and/or displacement of the preset cutting plane during the resection cutting, so that a repeat resection becomes necessary in the worst case.

DESCRIPTION OF THE INVENTION

A remedy is to be created here with this invention by refining a device of the type described in the introduction in that the device includes a base body that can be positioned on the bone as well as a cut-guiding body which can be attached to the base body in a variable position and has a cut-guiding structure for guiding a cutting tool in the cutting plane, where the cut-guiding body can be tilted relative to the base body by means of a first adjustable tilt mechanism about at least one axis for an angle adjustment of the cutting plane; and wherein the extent that the tilt mechanism is simple to operate and is reliable with regard to the accuracy of the position of the cutting plane, once its position has been set, even while performing the resection cut.

A solution to this problem is offered with the present invention through a device having the features a base body that can be positioned on the bone as well as a cut-guiding body which can be attached to the base body in a variable position and has a cut-guiding structure for guiding a cutting tool in the cutting plane, where the cut-guiding body can be tilted relative to the base body by means of a first adjustable tilt mechanism about at least one axis for an angle adjustment of the cutting plane; and wherein the tilt mechanism has a linear guide disposed on a first element of the device and has a linearly displaceable slide which can be displaced in the longitudinal direction along the guide and the tilt mechanism also has a guide section, with respect to which the slide moves, in displacement with an active section, on a second element of the device, which can be tilted about the first axis relative to the first element, wherein structures, acting together in the guide section and the active section, are formed, forming a sliding guide which acts transversely to the longitudinal direction.

The device according to the invention is thus characterized by a specially designed tilt mechanism, which has components on two elements that can be tilted about the first axis relative to one another. These elements may be the base body and/or the cut-guiding element directly, but these elements may also be and/or comprise bearing blocks that are provided for implementation of movability by several degrees of freedom and are also disposed between this base body and the cut-guiding element. Such bearing blocks may also be a component of the device according to the invention but need not.

According to the invention, a straight guide belonging to the tilt mechanism and a slide, which is linearly displaceable along this guide in its longitudinal direction, are situated on the first of the elements on which components of the tilt mechanisms are disposed. An active section is formed on the slide, sliding along the same in movement of the same with respect to a guide section, which is formed on the second element and belongs to the tilt mechanism, for example, by acting on same (but it can also move at a distance from same). Structures that interact with one another and form a sliding guide, which acts across the longitudinal direction of the guide, are formed in the guide section and the active section. Tilting of the first element relative to the second element about a first axis is achieved with this sliding guide in response to a linear displacement of the slide along the guide. The first element and the second element may therefore advantageously be connected to one another accordingly by means of an articulated connection that defines the first axis.

The design of the tilt mechanism, with a slide that is longitudinally displaceable along the guide, and a sliding guide operated by the former, is particularly easy to operate. In addition, in particular but not only when the slide is secured on the guide in a desired position with a force acting across the longitudinal direction of the guide, an unintentional release of the slide from the selected position, caused by vibration of a cutting device, is virtually impossible. This is the result of the angularity of the respective directions of movement, because to do so, the slide would have to be displaced by applying a force acting across the guide to the sliding guide in the longitudinal direction of the guide, but this would be an unfavorable force ratio for unintentional displacement. Moreover, with the implementation according to the invention, the dimensions of the individual element and their positions with respect to the axis of rotation may be selected, so that a force ratio is established such that a substantially greater force would have to be applied to tilt the one element relative to the other element on the cut-guiding element, more precisely the cut-guiding structure, than to the slide due to the comparatively great spacing of the slide from the axis about which the tilting occurs in comparison with a comparatively small spacing of the cut-guiding structure from this axis. This provides an additional safeguard in retention of the tilt position once it has been set with the slide.

The sliding guide may be designed to include a guide groove, which is inclined and/or curved with respect to the longitudinal direction, and a guide pin or guide peg, which is guided in this groove, are formed in the guide section on the active section of the slide. The guide groove or guide slot, on the one hand, and the guide pin and/or guide pin, on the other hand, then cooperate to form the sliding guide.

As already mentioned above, to retain the angular position once it has been set, the slide may be lockable in at least two different positions of the guide, for which purpose corresponding locking means are provided on the slide, and locking structures which interact with the former are provided on the guide. Locking means and locking structures are preferably formed so as to result in a plurality of locking positions, in which the slide can be locked in different longitudinal positions along the longitudinal direction of the guide.

According to another advantageous embodiment of the invention, the slide is releasably and removably disposed on the linear guide. This is advantageous in particular for cleaning and sterilization after the operation has been performed because the device according to the invention is provided for repeated use. For the same reason, it is preferable if, in the case of the device according to the invention, the individual parts that are movable in relation to one another are releasably connected to one another and can be separated easily for cleaning and sterilization purposes. This may be accomplished with regard to mutually tiltable elements, for example, by the fact that corresponding pivot axes are provided with flattened areas, and the axial guides are designed with an opening slot, which is provided in accordance with the diameter of the axis and is provided above the flattened areas. By tilting the two elements with respect to one another in such a way that the flattened areas become aligned with the opening, such elements can then be separated from one another easily. The separation of the slide from the linear guide and/or the other parts that are movable relative to one another is possible in a particularly advantageous manner and with a few simple manipulations.

A simple and robust design of both guide and slide is obtained when the linear guide has a guide rail with a rectangular, in particular square, cross section and the slide is designed like a sleeve with an internal contour, which corresponds to the cross sectional contour of the guide rail and is surrounded by a wall except for a continuous, slot-shaped opening, wherein the slot-shaped opening can be spread against a spring force exerted by the material due to the choice of the material and the wall thickness. Due to this design in particular, with suitably selected dimensions of the guide rail as well as the internal contour of the slide, it is possible to achieve a clamping and/or locking of the slide pushed onto the guide rail merely because of the spring force applied by the material. Thus, for example, no additional spring elements or similar small part structures are necessary here, which keeps the total number of assembled parts low on the one hand and thus minimizes manufacturing costs, but on the other hand, offers advantages, in particular with regard to postoperative cleaning and sterilization, and also eliminates the risk of losing any small parts in the surgical environment, or in the worst case, losing such a part and leaving it in the wound. For the locking effect, for example, corresponding protrusions, e.g., connectors, may be formed on the inside of the slide, such that they can engage in locking recesses formed along the rail. To permit simple displacement of the slide, the flanks of such locking protrusions or connectors may be beveled or designed with a sliding transition in the form of some other edge guides, so that they can slide over suitably tapered borders of the locking recesses by applying a force in excess of this retaining force.

In addition, it is advantageous if an angle scale is applied along the linear guide, and a pointer, which can be combined with the angle scale for reading. Thus, for a certain position of the slide in the longitudinal direction, an angle position of the cutting plane, which is thereby tilted about the first axis, can be read in relation to a predefined reference angle through the position of the pointer relative to the angle scale. Such an angle scale may be helpful, for example, in presetting a certain angle preoperatively, e.g., by imaging methods, for setting the angle of the cutting plane in tilting about the axis (e.g., setting a varus/valgus angle or setting a slope angle in the case of a resection to be performed for insertion of a knee endoprosthesis on the distal femur plateau or on the proximal tibia plateau). It is also possible to read a set angle by having the surgeon eyeball it and to compare it with suitably predetermined data to obtain an additional certainty and a reference.

For simple operability of the tilt mechanism, which is provided with the device according to the invention, it is advantageous if the sliding guide is designed so as to result in a linear conversion of the distance by which the slide is displaced to a tilt angle about which the cutting plane is tilted around the first axis. In other words, for tilting by one additional degree, a distance equal to that required for tilting by such a degree before or thereafter is required in displacement of the slide along the linear guide. This linear conversion gives the surgeon a better feel for the setting of an angle if he wants to work here according to a certain angle value or wants to make an initial presetting first.

In particular in cases in which tilting of the cutting plane not only about a single axis but also about two different axes is to be performed using a device according to the invention, for example, a setting of the varus/valgus angle, on the one hand, and of the slope angle, on the other hand, in adjusting the cutting plane for the resection on the proximal tibial plateau, a corresponding tilt mechanism like that provided above, i.e., a first and a second tilt mechanism, both of which have a linear guide and a slide, which together form a sliding guide in the manner described above, may be provided advantageously for each of the tilts to be performed and possible settings. The two tilt mechanisms are to be operated independently of one another for practical purposes. This is typically accomplished by the fact that at least one bearing block is situated between the base body and the cutting guide element, such that this bearing block is designed to be tiltable about a first axis relative to the base body and is supported on the base body, and the cut-guiding body is disposed on the bearing block accordingly, so that it can be tilted about a second axis, which is different from the first axis and is not parallel to it but in particular is perpendicular to it. In other words, with such an embodiment of the device according to the invention, two essentially similarly designed tilt mechanisms, each having a slide that is displaceable along a linear guide and a sliding guide designed with a guide section through interaction of an active section of the slide, such that two slides and/or sliding guides may be designed here, as explained above in greater detail.

To also be able to perform an adjustment of the position of the cutting plane with regard an additional degree of freedom by using the device according to the invention, a height adjusting unit may be provided, by means of which the cut-guiding body is linearly displaceable relative to the base body in a height direction and can be secured in its spacing from the former. This may be accomplished, for example, by inserting an additional bearing block in between, such that this bearing block is adjustable in height with respect to the base body and on which an additional bearing block or the cut-guiding body can be secured so that it can be pivoted about an axis. This height adjusting unit may advantageously be an adjusting screw for setting the spacing between the base body and the cut-guiding body. This adjusting screw may in particular be one having a small thread pitch to make it possible to perform a precision adjustment of the height adjustment and/or height setting. Here again, a scale may be provided, on the basis of which the surgeon can read the distance value between the base body and the cut-guiding body, for example.

The device according to the invention may be equipped as such a device in particular for bone resection on the proximal tibial plateau or as such a device for bone resection on the distal femur plateau.

In the case of a unit of the device for bone resection on the proximal tibia plateau, it can be provided with means for binding to an extramedullary aligning rod that is to be connected to a foot clamp, such that the base body can be positioned in a first approximate alignment by means of this aligning rod. It is also advantageously possible to connect this same device to an intramedullary reference, e.g., an aligning rod situated there, to thus give the surgeon working with this device a great variety in possible alignments and to allow him to work using the method he prefers and with which he is familiar. The device according to the invention may also contain a corresponding receptacle for a depth-finding rod, which makes it possible for the direction-finding///rod, which extends perpendicular to the set varus/valgus angle, to be received advantageously, in implementation for bone resection, on the proximal tibia plateau, to thereby allow the surgeon to make the alignment with regard to direction-finding in the direction of the respective foot and/or ankle.

BRIEF DESCRIPTION OF THE DRAWINGS

Additional advantages and features of the invention are derived from the following description of an exemplary embodiment on the basis of the accompanying figures, in which:

FIG. 9 shows a view of the upper section of the device according to the first exemplary embodiment, comparable to the view in FIG. 8, with a slope angle in deviation from 0°;

FIG. 10 shows a second exemplary embodiment of a device according to the invention for defining a cutting plane for bone resection, namely here for resection on the lower femur plateau without an attached cut-guiding block with the cut-guiding structure;

FIG. 11 shows a top view of the device according to the second exemplary embodiment in a 0° position selected with respect to the varus/valgus angle;

FIG. 12 shows a top of the second exemplary embodiment with the varus/valgus angle set in deviation from 0°;

FIG. 13 shows a perspective view of the second exemplary embodiment, and

FIG. 14 shows a perspective view of the second exemplary embodiment in a configuration on a femur and with the cut-guiding block attached.

The diagrams in the figures are schematic and are not necessarily drawn to scale.

METHOD(S) FOR IMPLEMENTING THE INVENTION

To describe the exemplary embodiments shown here, first with reference to FIGS. 1 to 9, a first exemplary embodiment of the invention is described, illustrating a device for adjustable definition of the cutting plane of the resection cut on the upper tibia plateau.

Figure 1:
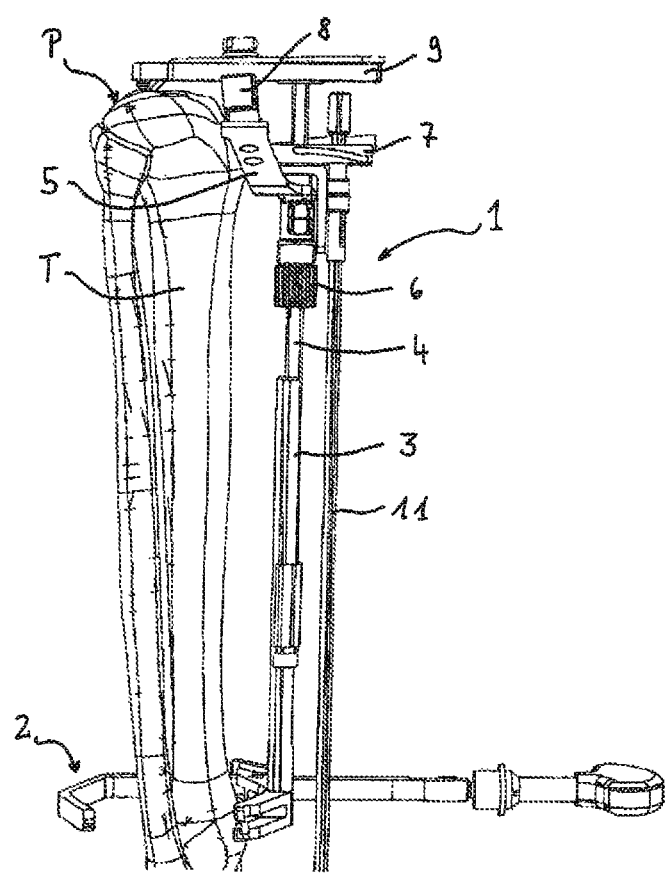
FIG. 1 shows a diagram of a first exemplary embodiment of a device according to the invention for defining a cutting plane for bone resection, namely here for bone resection on the upper tibia plateau in a schematic configuration on a tibia.

With reference to FIG. 1, such a device for defining a cutting plane for tibia resection in a schematic configuration on a tibia bone, in particular its tibia T is shown and is labeled as device 1 in general. Device 1, which is of course not disposed on a completely exposed tibia T in the actual use but instead is disposed on a lower leg bone, in which only the region of the knee that is to be operated on is exposed, comprises a foot clamp 2, with which it can be secured on a patient's leg with a lower section in the area of the ankle. Starting from the foot clamp 2 and fixedly attached thereto, a receiving tube 3 extends away from the foot clamp 2; an aligning rod 4 is accommodated and guided linearly in a telescoping manner in said receiving tube. A yoke-shaped base body 5, on which a first bearing block 17 is disposed in turn (cf. FIG. 4), is connected to the aligning rod 4; this bearing block is movable in the longitudinal direction of the aligning rod 4 for precision adjustment of a height setting in the longitudinal direction by means of a screw sleeve 6 in relation to the base body 5 and is adjustable in a position.

A second bearing block 7 is attached to the first bearing block 17 and can be rotated in relation thereto, for setting a varus/valgus angle in a manner to be explained in greater detail below. A cut-guiding block 8 is in turn supported on the bearing block 7—again rotatable about an axis, this time to adjust a slope angle. Furthermore, a clamp strap disposed on the upper end of the aligning rod 4 can also be seen, having a mandrel 10, which is not visible here but can be seen in FIG. 3 in particular, on its section resting on the plateau P of the tibia T, so that it can be hammered into the tibia plateau with this mandrel. Thus, in the wake of a first presetting of the device 1 according to the invention on the lower section of the tibia T, the foot clamp 2 provides initial support, in particular a lateral fixation on the upper section of the tibia T for the clamp strap 9.

Furthermore, a direction-finding rod 11, which is suspended in the bearing block 7 and serves as a direction-finding aid for the adjustment of the varus/valgus angle, can also be seen.

Figure 2:
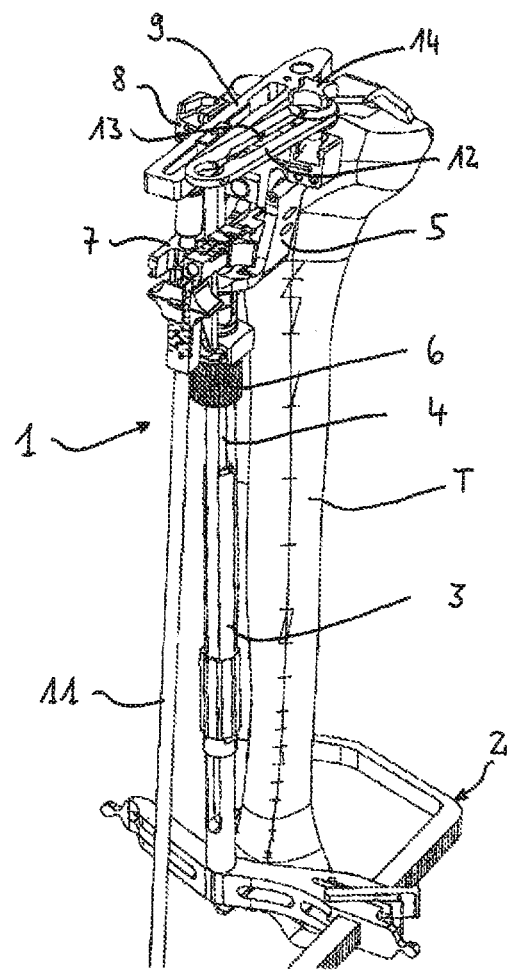
FIG. 2 shows the device according to the exemplary embodiment from FIG. 1 in a similar arrangement as seen from another perspective.
Figure 4:
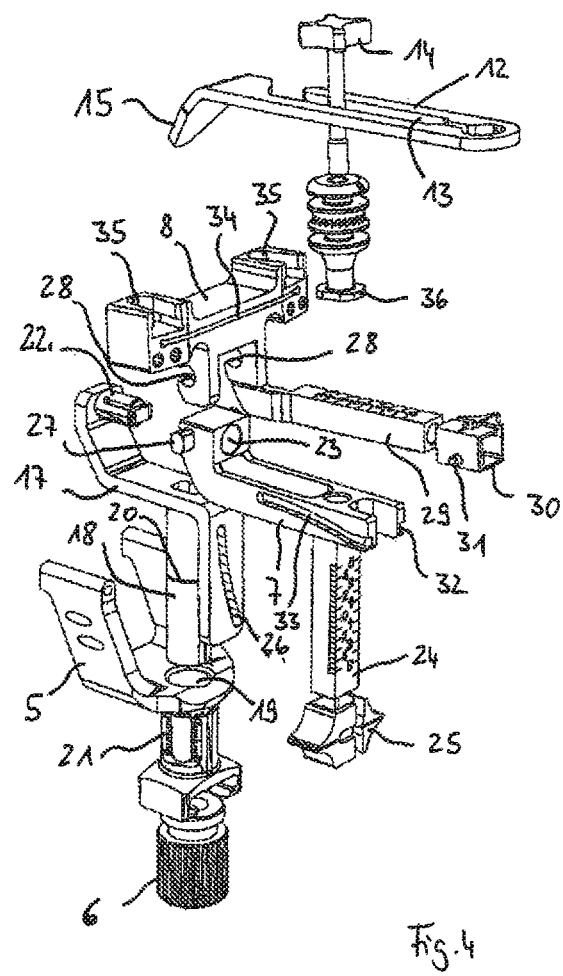
FIG. 4 shows additional elements of the exemplary embodiment of the device according to FIGS. 1 and 2 in an exploded diagram.

FIG. 2 shows the device from FIG. 1 again from a different perspective, a condyle caliper 12, which is attached to the cut-guiding block 8, being secured here again; the condyle caliper 12 can be releasably secured on the cut-guiding block 8 and can be displaced in a longitudinal position by means of a longitudinal slot 13 formed in the condyle caliper 12, through which a connecting screw 14 is guided. The condyle caliper 12 has a cropped front end 15, as shown in FIG. 4 in particular, forming the caliper tip of the condyle caliper 12. In this application, this probe tip is placed on the lowest point on the worn condyle in order to determine the cutting height of the resection cut on the tibia plateau starting from there.

Figure 3:
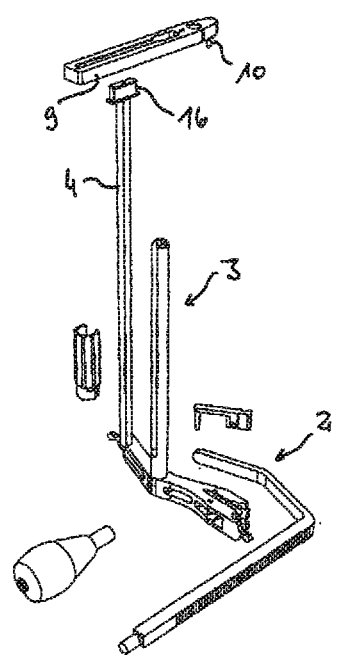
FIG. 3 shows an exploded diagram of parts of the device according to the exemplary embodiment in FIGS. 1 and 2.

FIG. 3 shows individual elements of the foot clamp 2 with the receiving tube 3 disposed thereon as well as the aligning rod 4 and the clamp strap 9, which is to be releasably disposed on the aligning rod 4. This also shows that the clamp strap 9 can be easily and releasably secured on this upper end of the aligning rod 4 by simply placing a T-shaped connecting piece 16 on the upper end of the aligning rod 4.

FIG. 4 shows the components of the device 1, which are disposed on its upper end, shown here again in an exploded diagram. This enlargement serves also in particular to illustrate the mechanism of action for the adjusting means according to the invention, for adjusting the varus/valgus angle and/or the slope angle to be selected for defining the cutting plane.

It can be seen well here that this upper part of the device according to the invention is made up of four main components, namely the yoke-like base body 5, the first bearing block 17, which is attached to the latter, the second bearing block 7 and the cut-guiding block 8. The first bearing block 17 has a hollow rod 18, with which it is disposed in a rotationally fixed manner in a rod receptacle 19 on the base body 5. The hollow rod 18 can be moved up and down in its longitudinal direction in the rod receptacle 19 by means of the screw sleeve 6 for precision adjustment of the resection cut height, which is determined by the corresponding longitudinal distance between the base body 5 and the first bearing block 17. To ensure that checking a setting will be simplified here, a reference line 20 is placed on the hollow rod 18 as a marker, which is recognizable through an inspection window in the rod receptacle 19 and coincides with a scale 21, on which a positioning and/or longitudinal displacement of the bearing block 17 with respect to the base 5 can be read, e.g., in the millimeter range.

A pivot pin 22, whose alignment runs perpendicular to the longitudinal direction of the hollow rod 18, is disposed on the bearing block 17. The bearing block 7 sits on this pivot pin 22 with a hole 23 and is thus rotatable relative to the bearing block 17 about an axis of rotation defined by the longitudinal axis of the pivot pin 22. For setting an angle in this regard, which reflects the varus/valgus angle of the cutting plane, a linear guide path 24, which is in a normal position in the assembled state, extending approximately along the longitudinal direction of the hollow rod 18, is disposed on the bearing block 7. A slide 25 having an approximately G-shaped cross section, i.e., having an opening slot on its top side, is pushed onto this linear guide path 24 having a rectangular cross section. A guide pin which engages in a guide groove 26 on the bearing block 17 is integrally molded (not shown here) into the rear of this slide 25. This guide groove 26 runs along a curved path at an inclination in comparison with the longitudinal axis of the hollow rod 18. Acting together with the rod situated on the slide 25, this guide groove 26 forms a sliding guide, which causes a rotation of the bearing block 7 about the pivot pin 22 on the bearing block 17 in a longitudinal displacement of the slide 25 along the linear guide path 24. The slide 25 is formed, in its dimensions and its relationship to the external shape of the linear guide path 24, so that it can be displaced along this path, but it remains in a position once it has assumed that position because of its clamping forces applied due to the material itself. This is further supported by locking means, which are described in further detail below. A scale on the linear guide path 24, in conjunction with a corresponding mark on the slide 25, facilitates a reading of the current setting of the rotational angle of the bearing block 7.

Moreover, swivel pins 27 are disposed on the bearing block 7 (at both sides of the hole 23), but only one swivel pin is labeled with a reference numeral in this figure), by means of which the cut-guiding block 8 is guided and supported, so that it can be pivoted about the axis formed by the swivel pin 27 with corresponding pivot bearings 28. The alignment axis of the swivel pin 27, which defines the pivot axis, is perpendicular to the direction of the pivot pin 22. An adjustment of the slope angle is achieved by corresponding pivoting of the cut-guiding block 8 about the pivot axis provided by the swivel pin 27. A second linear guide 29 is integrally molded on the cut-guiding block 8; a slide 30 is guided so that it can slide and be displaced by means of this guide. This slide 30 also has a G-shaped sectional profile; with regard to its dimensions, with respect to the thickness of the material and the choice of material, and in relation to the essentially square cross-sectional shape of the linear guide 29, it is selected so that it remains in a clamping position on the linear guide 29 once it has assumed that position, with locking means providing additional support here. A pin 31, accommodated and guided in a guide groove 32 on the bearing block 7, is integrally molded on an active surface on the slide 30. The guide groove 32 has a course similar to that of the opposing guide groove 33, so it is also curved and, together with the guide pin 31, forms a sliding guide, which causes displacement of the slide 30 along the linear guide 29 to result in pivoting of the cut-guiding block 8 about the pivot axis formed by the alignment of the swivel pin 27.

This diagram also shows a cut-guiding slot 34, designed in the cut-guiding block 8, which serves to guide a cutting tool for placement of the resection cut. Finally, this also shows receptacles 35 disposed on the top side of the cut-guiding block 8, serving to receive a connecting piece 36 for connection to the condyle caliper 12. Through positioning of the receptacles 35 on the right and left sides, respectively, of the cut-guiding block 8, the condyle caliper 12 can be set on the interior and/or exterior condyle of the respective tibia plateau, depending on which of the two condyles shows greater wear and serves as a reference for the height adjustment.

The adjusting mechanisms for adjusting the varus/valgus angle and the slope angle using the device according to the invention by means of the linear guides 24 and/or 29 and the slides 25 and/or 30, which can be moved on these guides and, together with the curved guide grooves 26 and/or 32 and the guide pins 31 disposed on the slides 25, 30, can cause the sliding guide to be adjusted. This type of adjustment possibility is especially compact structurally and can be achieved with only a few parts that are easy to design. It is reliably stable in particular, once it has assumed a position, which is of enormous importance in positioning the resection cutting plane through corresponding adjustment of the cut-guiding block 8 with the cut-guiding slot 34 in order to prevent a change in position of the cut-guiding block 8, and thus of the cut-guiding slot 34, during an operation in performing the resection cut, for example.

FIG. 5 shows again a view of the upper section of the device 1 (cf. FIG. 1) in the assembled state, but the condyle caliper is not shown here, and instead, the clamp strap 9 with the mandrel 10 situated on the upper end of the aligning rod 4 is shown. This also shows how the two linear guides 24, 29, with the slides 25 and 30, respectively, disposed thereon, are situated close to and opposite the respective sections with the guide grooves of the bearing blocks 17 and 7, respectively, to thereby permit an interaction of the sliding guide and the corresponding angle setting.

Figure 6:
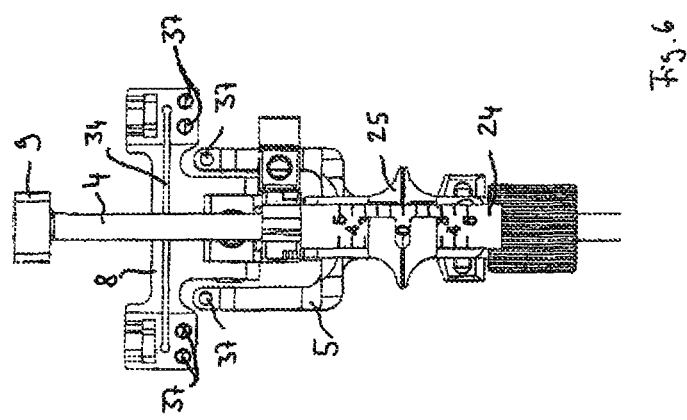
FIG. 6 shows a top view of the upper region of the exemplary embodiment according to FIG. 1 in an untilted 0° position of the varus/valgus angle.
Figure 5:
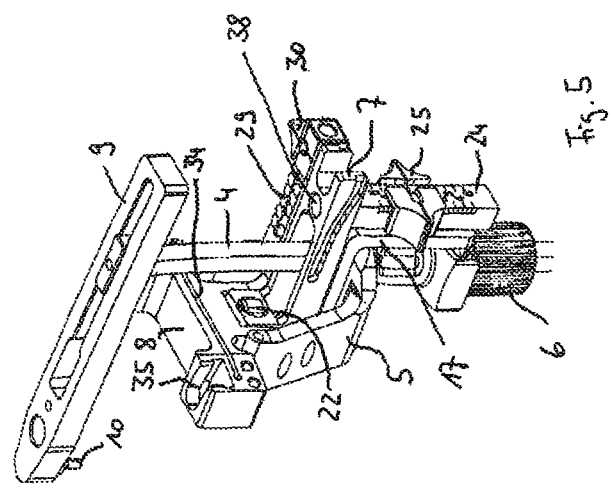
FIG. 5 shows the upper section of the device according to the exemplary embodiment in FIG. 1 in an assembled form but without the attached probe for the condyle.
Figure 7:
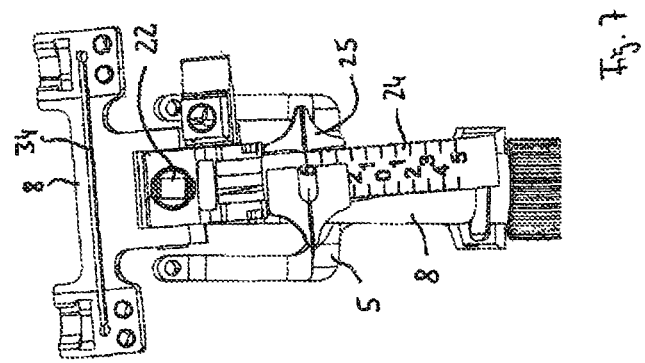
FIG. 7 shows a view comparable to that in FIG. 6 but with a varus/valgus angle set in deviation from 0°.

FIGS. 6 and 7 show a view of the upper section of the device according to the invention—shown in one case with the aligning rod 4 and the clamp strap 9 disposed thereon (in FIG. 6) and in the other case without these elements. The varus/valgus angle is set at 0° in FIG. 6. The setting selected for FIG. 7 shows the maximum leftward tilt. This shows well how the guide block 8 is inclined relative to the longitudinal axis of the journal receptacle on the base body 5 and therefore is also moved to adjust the varus/valgus angle in accordance with the cut-guiding slot 34.

Figure 8:
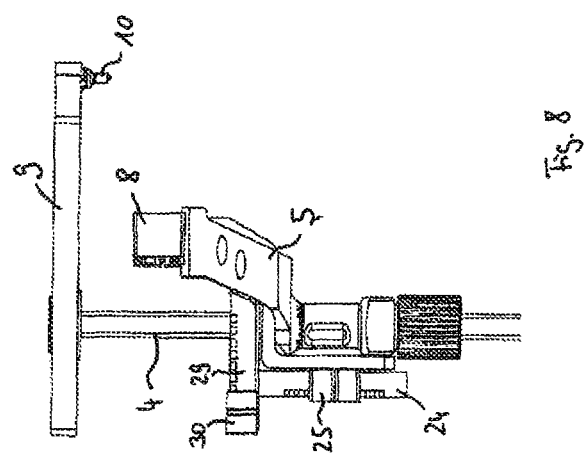
FIG. 8 shows a diagram of the upper section of the first exemplary embodiment shown in FIG. 5 for a device according to the invention with a 0° setting, selected with respect to the slope angle.

FIGS. 8 and 9 show two different side views: FIG. 8 shows the aligning rod 4 with the clamp strap 9 disposed thereon; FIG. 9, without these elements, shows the parts disposed at the upper end of the device, once in the zero position for the slope angle and once in a position inclined to adjust the slope angle. In FIG. 9 the slope angle is not determined by inclination but instead the varus/valgus angle is adjusted; it deviates from the zero position as shown in FIG. 8. Both figures show clearly that the cut-guiding block 8 can be tilted with respect to the base. In FIG. 9 it is shown with a downward inclination to the right (to thus adjust the slope angle).

Here again, the locking grooves introduced laterally into the linear guides 24 and 29 can also be seen. Corresponding locking connectors and/or locking protrusions for holding the position can engage in these locking grooves. In addition, these locking grooves offer a tactile positioning aid, which enable the surgeon to estimate the angle adjustment by counting out audible and tactile engagement procedures and thereby estimating an adjustment distance and/or angle for the corresponding adjustment of the varus/valgus angle and/or slope angle.

The device 1 (cf. FIG. 1) can be broken down into its components with simple manipulations, which may even be performed during surgery to some extent. Pinholes 37 (cf. FIG. 6) are provided on the base and on the cut-guiding block 8, so that fastening pins can be guided through these pinholes in a known way and inserted into holes created in the bones accordingly. If the base body 5 is secured on the bone with corresponding pins, the aligning rod 4 and the clamp strap 9 may be removed, for example, and the foot clamp 2 may also be removed. If the cut-guiding block 8 is still correctly positioned after having set the cutting height, the varus/valgus angle and the slope angle, then pins can be pushed through the corresponding pinholes 37 on this element, pushing them into previously created holes in the bone and anchored there, so that the cut-guiding block 8 is secured in its alignment. Then the additional elements, including the bearing block 7, may be removed even during surgery, so that ultimately only the cut-guiding block 8 remains on the bone and very few parts of the device according to the invention are in the way when initiating the resection cut. However, the surgeon will of course also have left other elements of the device in the structure while initiating the resection cut, up to and including a complete structure, including the foot clamp. The form of usage here is ultimately the surgeon's choice.

In the adjustment of the varus/valgus angle, the direction-finding rod 11, which is guided through an opening 38 (cf. FIG. 5) into the bearing block 7, can support the surgeon in that the surgeon makes an alignment with respect to the tibia, i.e., the lower leg using this direction-finding rod 11.

The device 1 according to the invention, together with all its elements, is preferably produced from a biocompatible material, in particular stainless steel, and its shape is such that simple cleaning and sterilization can be performed for reuse after surgery. It also has only a few parts with comparatively large dimensions due to the type of design, in particular the type of design of the adjustment options for varus/valgus angles and slope angles, so that there are no small screws or the like that need be disinfected and cleaned or that might become lost during surgery, possibly, in the worst case, even remaining in the wound after treatment.

Additional advantages with regard to accuracy and ease of handling in adjustment and/or definition of the cutting plane for the section cut are also obtained by shifting all the adjustment options, i.e., the adjustment options of the varus/valgus angle and the slope angle, as well as ultimately the precision adjustment with regard to the cutting height, to the upper end of the device 1, i.e., eliminating the adjustment in the area of the foot clamp 2, which is performed in some of the approaches from the prior art.

Finally, it should also be pointed out that a device having the components to be disposed in the upper region of the tibia T may also be used in an intramedullary fastening, i.e., with attachment to a journal inserted into the tibia plateau in the direction of the medullary channel, and secured there. A retaining strap would then be provided accordingly instead of the clamp strap 9, the retaining strap being attached to the journal introduced into the tibia, on the one hand, and having an aligning rod 4, on the other hand. With such a type of fixation, it may optionally be possible to omit a foot clamp 2, because adequate stability is frequently already achieved with the intramedullary attachment.

A second exemplary embodiment of a device according to the invention for aligning the resection cut on the lower femur plateau will be explained below with reference to FIGS. 10 through 14.

FIG. 10 shows a schematic diagram of an assembly on the lower plateau of a femur F, showing an aligning part 40 of a device according to the invention according to a first exemplary embodiment. This aligning part 40 has a base body 41, which at the same time forms a linear guide path 42 in an important section. The base body 41 is provided with a continuous longitudinal hole 52 (cf. FIG. 13) in its interior, through which a support rod 43 protrudes and is secured in a fixed position on the femur F in a medial hole. Thus the base body 41 is disposed in a fixed position relative to the femur F. On its end remote from the femur, the base body 41 has swivel pins 44 with which it engages in a slot-shaped pin receptacle 45 in a bearing block 46 and can be pivoted with respect to that and/or accommodates the bearing block 46 pivotably therein.

A slide 47, which is disposed on the linear guide path 42, has been shaped and designed with a G-shaped profile in a manner comparable to that of the slides 25 and/or 30 in the exemplary embodiment, such that it can sit on the linear guide path 42 with a clamping seat. The slide 47 has, on its rear side (not visible here) in an active section, a guide pin, with which it is seated and is guided in a guide groove, which is also covered by the linear guide path 42, as shown in FIG. 10. This guide groove is formed on a section of the bearing block 46 and is in mirror image to the longitudinal axis of the section to an additional guide groove 49, which can be seen here. The guide groove 48, with the slide 47 running in it, in the alignment shown in FIG. 10, can be seen in FIG. 11 with its integrally molded pin.

With the detail of the device shown here, the varus/valgus angle can be determined for the determination of the resection cutting plane on the femur plateau. This functions in the same way as the adjustment of the angle in the first exemplary embodiment described above. Here again, the journal integrally molded on the slide 47 runs in the guide groove 48, which has a curved path. This interaction therefore results in a sliding guide, which causes a pivoting of the bearing block 46 with respect to the base body 41 about the pivot axis formed by the swivel pin 44. The bearing block 46 is therefore adjusted according to a varus/valgus angle that is to be selected. The cut-guiding block (not shown here) is placed over the openings, which, in the section of the bearing block 46 near the femur, are labeled as R and L (these designations are used for the right and left leg, respectively, because these components can be used for both applications). The cut-guiding block is connected using corresponding journals in these openings in such a manner that it can no longer be shifted transversely to do so. The cut-guiding block (not shown here) has a cut-guiding slot in the usual manner, serving to guide a cutting tool to create the resection cut.

This also shows a scale applied to the linear guide path 42 with angle data indicating a deviation in the varus/valgus angle from the 90° position. This also shows that the letters "R" and "L" are provided on the slide in mirror-inverted arrangement. This again indicates the universal applicability of this device. With the alignment shown in FIG. 10 (also in the other drawings), the device is set for use on the right leg. If the resection cutting plane is mapped for the femur plateau of the left leg, then the slide 47 must be loosened by removing the linear guide path 42 and then rotated, so that the letter L appears correctly and legibly in a view according to FIG. 10, and then the slide is pushed again onto the linear guide path 42. In doing so, the guide pin, which is integrally molded on the rear of the slide, no longer engages in the guide groove 48, but instead engages in the guide groove 49, which is designed in mirror image on the side of the bearing block shown at the left in FIG. 10. A pivoting of the varus/valgus angle in the other direction for the adjustment on the left leg is made possible in this way.

The degree numbers shown on the scale indicate here the actual deviations from the 90° position in degrees, for which the linear guide of the guide groove 49 is calculated and selected, so that with an equidistant displacement of the slide 47 from one scale part to the next, there is always an adjustment of the inclination by 1° about the swivel pin 44, while at the same time, there is an adjustment of the varus/valgus angle by 1°.

FIGS. 11 and 12 show the aligning part 40 once in a position for an untilted varus/valgus angle (90° to the longitudinal axis of the femur F), in FIG. 12 with a deviation and/or tilt of this angle by 7° from this normal position for the right leg. This shows clearly the angle assumed between the base body 41 and the bearing block 46, to which the actual cut-guiding block is added (not shown here).

Finally, FIG. 13 shows again, in a perspective view, the aligning part 40 in the normal position of an alignment of the varus/valgus angle perpendicular to the longitudinal axis of the femur F. This diagram shows especially well the locking notches 50, which are disposed in equidistant intervals along the linear guide path 42 and engage in the corresponding protrusions 51 on the slide 47 when the respective position has been reached. This also shows well the central longitudinal bore 52 in the base body 41 through which the support rod 43 protrudes in the application case (cf. FIG. 10).

Finally, FIG. 14 shows how a cut-guiding block 53 is disposed on the bearing block 46 on its thickened end, which is in contact with the femur F, and how it is secured there by means of a hole and pin fastening. The cut-guiding block 53 has a cut-guiding slot 54 for guiding the blade of a cutting tool. Furthermore, this also shows pinholes 37 through which fastening pins can be guided into holes created in the femur F for securing the cut-guiding block 53 on the femur F. The cut-guiding block 53 is typically not positioned until after adjusting the varus/valgus angle but it may also be applied prior to that.

This second exemplary embodiment also shows an element of a simple design, made up of a few parts that are comparatively simple to handle and can easily be released from one another for the purposes of cleaning of sterilization. Here again, the precise setting of the angular position of the resection cutting plane is maintained even under stress, for example, due to vibrations during a resection cut. All the elements of this device are also made of a biocompatible material, in particular stainless steel.

The exemplary embodiments described above are not restrictive and serve only to illustrate the invention. In particular the invention is not limited only to such applications for mapping and positioning of the resection cutting plane in the area of the femur plateau and/or the tibia plateau. Other resection cutting planes may also be mapped onto other bones, for example, on the head of the humerus. The device need only be adjusted accordingly for this, wherein the angular adjustment may be made in the manner according to the invention.

LIST OF REFERENCE NUMERALS

1 Device for defining a cutting plane for tibia resection
2 Foot clamp
3 Receiving tube
4 Aligning rod
5 Base body
6 Screw sleeve
7 Bearing block
8 Cut-guiding block
9 Clamp strap
10 Mandrel
11 Direction-finding rod
12 Condyle caliper
13 Longitudinal slot
14 Connecting screw
15 Cropped front end
16 T-shaped connecting piece
17 Bearing block
18 Hollow rod
19 Journal receptacle
20 Reference line
21 Scale
22 Pivot pin
23 Hole
24 Linear guide path
25 Slide
26 Guide groove
27 Swivel pin
28 Pivot bearing
29 Linear guide
30 Slide
31 Guide pin
32 Guide groove
33 Guide groove
34 Cut-guiding slot
35 Receptacle
36 Connecting piece
37 Pinhole
38 Opening
40 Aligning part
41 Base body
42 Linear guide path
43 Support rod
44 Swivel pin
45 Pin receptacle
46 Bearing block
47 Slide
48 Guide groove
49 Guide groove
50 Locking notch
51 Locking protrusion
52 Longitudinal bore
53 Cut-guiding block
54 Cut-guiding slot
F Femur
P Plateau
T Tibia

The invention claimed is:

1. A device for adjustable definition of a cutting plane for a bone resection, the device comprising:
a base body that is adapted to be positionable on the bone; and
a cut-guiding body which is mounted so as to be variable in position on the base body; and wherein the cut-guiding body has a cut-guiding structure for guiding a cutting tool in the cutting plane, wherein the cut-guiding body is tiltable relative to the base body by a first adjustable tilt mechanism about at least a first axis in order to adjust an angle of the cutting plane;
wherein the first tilt mechanism has:
a first linear guide arranged on a first element of the cut-guiding body; and
a first slide which is linearly displaceable along the first linear guide in the longitudinal direction thereof, and wherein the first tilt mechanism also has a second element of the cut-guiding body tiltable relative to the first element about the first axis,
a first guide section opposite to a second guide section upon which the first slide moves with an active portion during the displacement, wherein interacting structures are formed in the first guide section and in the active portion and form a slotted guide which acts transversely with respect to the longitudinal direction; and wherein the device further comprises:

a first guide groove in the first guide section, wherein the first guide groove is curved with respect to the longitudinal direction; and a guide pin engaging in the first guide groove and guided therein on the active portion of the first slide.

2. The device according to claim 1, further comprising locking structures in an area of the first linear guide which interact with a locking member on the first slide, and wherein the first slide is securable by locking in at least two different positions on the first linear guide.

3. The device according to claim 1, wherein the slide is arranged on the first linear guide, so that the slide is releasable and removable therefrom.

4. The device according to claim 1, wherein the first linear guide is a guide rail having a rectangular cross-sectional contour and the first slide is shaped like a sleeve with an inside contour which corresponds to the cross-sectional contour of the guide rail and is surrounded by a wall except for a continuous slot-shaped opening, wherein through the choice of the material and of the wall thickness, the slot-shaped opening is expandable counter to a spring force exerted by the material.

5. The device according to claim 4, wherein the guide rail has a square cross-sectional contour.

6. The device according to claim 1, wherein an angle scale is disposed along the first linear guide, and a pointer that is alignable with the angle scale for reading off is disposed on the first slide such that for a defined position of the first slide in the longitudinal direction, a pointer position makes it possible to read off an angle position of the cutting plane thus tilted about the first axis in relation to a predefined reference angle.

7. The device according to claim 1, wherein the slotted guide is designed to allow a linear conversion of the distance by which the first slide is displaced to a tilt angle by which the cutting plane is tilted about the first axis.

8. The device according to claim 1, wherein the cut-guiding body is additionally tiltable relative to the base body about a second axis that is not parallel to the first axis, and for tilting about the second axis, a second adjustable tilt mechanism is provided that is operable independently of the first adjustable tilt mechanism and wherein the second tilt mechanism has:

a second linear guide arranged on a first element; and a second slide which is linearly displaceable along the second guide in the longitudinal direction thereof, and wherein the second tilt mechanism also has, on a second element tiltable relative to the first element about the second axis, a second guide section opposite which the second slide moves with a second active portion during the displacement, wherein interacting structures are formed in the second guide section and in the second active portion and form a slotted guide acting transversely with respect to the longitudinal direction;

a second guide groove in the second guide section, wherein the second guide groove is curved with respect to the longitudinal direction; and a second guide pin engaging in the second guide groove and guided therein on the second active portion of the second slide.

9. The device according to claim 1, wherein the device further comprises a height adjustment mechanism that linearly moves the cut-guiding body in a vertical direction relative to the base body and is securable at this spacing from the latter.

10. The device according to claim 9, wherein an adjusting screw for adjusting the distance between the base body and the cut-guiding body is provided in the height adjustment mechanism.

11. The device according to claim 1, wherein the device is configured for bone resection on the proximal tibia plateau.

12. The device according to claim 1, wherein device is configured for bone resection on the distal femur plateau.

* * * * *